United States Patent [19]

Schael

[11] 4,267,041
[45] May 12, 1981

[54] APPARATUS FOR THE ULTRAFILTRATION CONTROL IN CONNECTION WITH THE HEMODIALYSIS

[75] Inventor: Wilfried Schael, Bad Homburg von der Hohe, Fed. Rep. of Germany

[73] Assignees: Eduard Fresenius; Chemisch-pharmazeutische Industrie KG, Apparatebau KG, Bad Homburg, Fed. Rep. of Germany

[21] Appl. No.: 83,321

[22] Filed: Oct. 10, 1979

Related U.S. Application Data

[63] Continuation of Ser. No. 925,984, Jul. 19, 1978, abandoned.

[30] Foreign Application Priority Data

Jul. 30, 1977 [DE] Fed. Rep. of Germany ....... 2734561

[51] Int. Cl.$^3$ .............................................. B01D 31/00
[52] U.S. Cl. ................................. 210/109; 210/195.2; 210/257.2; 210/321.3
[58] Field of Search ............... 210/109, 138, 142, 143, 210/194, 257.2, 321 A, 321 B, 195.2, 416 R, 258, 321 R, 433 M, 116; 137/99, 118, 119

[56] References Cited

U.S. PATENT DOCUMENTS

| | | | |
|---|---|---|---|
| 3,489,159 | 1/1970 | Cheng et al. | 210/416 R X |
| 3,697,418 | 10/1972 | Johnson | 210/321 B |
| 3,774,762 | 11/1973 | Lichtenstein | 210/94 |
| 3,939,069 | 2/1976 | Granger et al. | 210/22 A |
| 3,946,731 | 3/1976 | Lichtenstein | 210/87 X |
| 3,979,284 | 9/1976 | Granger et al. | 210/22 A |
| 4,096,059 | 6/1978 | Pinkerton | 210/22 A |
| 4,113,614 | 9/1978 | Rollo et al. | 210/22 A |
| 4,118,314 | 10/1978 | Yoshida | 210/22 C |
| 4,190,536 | 2/1980 | Grimsrud | 210/93 |

FOREIGN PATENT DOCUMENTS

| | | | |
|---|---|---|---|
| 832648 | 12/1975 | Belgium | 210/321 B |
| 2552304 | 5/1977 | Fed. Rep. of Germany | 210/321 B |
| 7701451 | 5/1977 | Netherlands | 210/321 B |

OTHER PUBLICATIONS

Perry, R. et al., Chemical Engineer's Handbook, McGraw-Hill Book Co., New York, 1973, pp. 16-22 to 16-38.

*Primary Examiner*—Charles N. Hart
*Assistant Examiner*—David R. Sadowski
*Attorney, Agent, or Firm*—W. G. Fasse; D. F. Gould

[57] ABSTRACT

An apparatus for controlling the ultra-filtration in connection with a hemodialysis treatment comprises a plurality of storage containers for the dialysis liquid. These containers are connected in parallel to each other and to the circulatory system of the dialysis liquid by groups of valves which are controlled by an automatic timer mechanism in such a manner that these containers are operatively connected to the circulatory system in a timed sequence. The groups of valves are operatively connected to the inlet and outlet ports of these containers. In addition to the main pump for circulating the dialysis liquid, there is a branching pump for withdrawing a dialysis liquid proportion from the system and a pump for filling the containers with a fresh dialysis liquid.

6 Claims, 3 Drawing Figures

APPARATUS FOR THE ULTRAFILTRATION CONTROL IN CONNECTION WITH THE HEMODIALYSIS

This is a continuation of application Ser. No.: 925,984 filed: July 19, 1978, now abandoned.

BACKGROUND OF THE INVENTION

The present invention relates to an apparatus for controlling the liquid withdrawal from a dialysis circulatory system in connection with a hemodialysis treatment operating as an artificial kidney. This apparatus shall be suitable as a component of a complete dialysis apparatus and also as an attachment to devices which heretofore have been operated without controlling the liquid withdrawal from the circulatory system.

As is known, a hemodialysis treatment comprises mainly the step of guiding the blood of the patient to be treated along a surface of a semi-permeable membrane while an aqueous solution of a suitable composition flows in a counter current flow thereto on the other side of the membrane. Substances which normally ought to be discharged through the kidneys, enter by diffusion from the blood through the membrane into the dialysis solution and are removed along with the latter. Besides such removal of urine bound or urenic substances, it is also necessary to withdraw from the patient whose kidney function has stopped, a certain quantity of water, in order to normalize the patient's liquid balance.

In substantially all of the hemodialysis devices which have been used heretofore, said liquid withdrawal is adjusted by the presetting of a pressure difference between the blood side of the semi-permeable membrane and the dialysis solution side of the membrane, whereby the fact is utilized that an increasing liquid quantity passes through the membrane with an increasing pressure difference across the membrane. However, the ultrafiltration characteristic of the membranes, that is, the relationship between the pressure across the membrane and the liquid passage therethrough per unit of time is subject to substantial variations from membrane specimen to membrane specimen. Said relationship is further influenced by the time changes in the membrane permeability due to deposits of blood components so that for these reasons alone said method exhibits large inaccuracies. In addition, the influence of the fluctuations of the blood pressure must be taken into account since these fluctuations cause corresponding fluctuations of the pressure across the membrane.

A frequently used method for controlling the liquid withdrawal comprises continuously monitoring the weight of the patient during the treatment by means of an in-bed scale. This operation, however, involves a substantial effort and expense because the price of an in-bed scale is approximately of the same order as the price of a hemodialysis apparatus. Thus, different suggestions have been made and some of them have been carried into practice, which aim at integrating the measuring or the control of the liquid withdrawal into the function of the hemodialysis apparatus.

One of these prior art methods makes it possible to indicate the actual value of the rate of liquid withdrawal by actuating a selector switching device. This is accomplished in that the influx of the dialysis solution is shut off while maintaining the pressure across the membrane and inserting into the discharge pipe a flow meter from which the instantaneous liquid withdrawal rate may be read. However, a continuous measuring is not possible according to this principle because it requires an interruption of the normal operation.

Another known method provides filling the entire dialysis solution supply into a closed, rigid storage container and to return the used-up dialysis solution into the same storage container. The desired liquid quantity per unit of time is withdrawn from this system having a constant volume, by means of a pump having an adjustable feed rate. Due to the fact that the total system is unyielding, the withdrawn liquid quantity must correspond to the liquid quantity which entered from the blood through the membrane into the dialysis solution circuit. An essential disadvantage of this method resides in the fact that the available volume of dialysis solution is limited to the volume of the storage container.

Another disadvantage of the just mentioned prior art is the fact that the efficiency decreases constantly during the treatment because fresh and used-up dialysis solution intermix.

The method described in the just preceding paragraph has been further developed in that a smaller container is used while working in accordance with the same principle and periodically renewing the content of the smaller container at relatively short time intervals. This is accomplished by quickly emptying the container after a predetermined length of time and newly filling it, whereby a buffer container is connected in series in order to keep available a sufficient liquid volume for the rapid filling. However, the loss of time resulting from the emptying and filling of the container can, nevertheless, not be reduced at random and constitutes a disadvantage in any event.

Other methods aim at providing a "dynamically rigid" system in order to withdraw liquid from the system in a defined manner as described above with regard to the rigid container. This may be accomplished in that with suitable technical means a conformity between the through flow rates in the supply and discharge of the dialysis solution is enforced which conformity is as exact as possible. In principle this may take place, for example, by means of two synchronized pumps in the supply and discharge conduits. However, the requirements regarding the accuracy are very high and the resulting technical expenditure is substantial.

OBJECTS OF THE INVENTION

In view of the above it is the aim of the invention to achieve the following objects singly or in combination:

to avoid the mentioned disadvantages, more specifically, to provide a relatively simple apparatus by means of which the liquid withdrawal from a dialysis circulatory system may be exactly predetermined and continuously controlled;

to provide a liquid withdrawal control apparatus which may be either an integrated component of a hemodialysis device or which is useable as an attachment for hemodialysis devices;

to enable the continuous, uninterrupted liquid withdrawal control from a hemodialysis circulatory system without influencing the dialysis operation as such;

to control the switching of storage containers into and out of a hemodialysis circulatory system in a predetermined automatically timed sequence; and to use storage containers which are so constructed that a substantially laminar liquid exchange flow is established.

SUMMARY OF THE INVENTION

According to the invention there is provided an apparatus for the ultrafiltration control in connection with a hemodialysis treatment which is performed with a supply quantity of a dialysis liquid and which uses a branching pump for withdrawing of a predetermined proportion of the dialysis liquid out of the circulatory dialysis system, wherein several storage containers are connected in parallel into the circulatory system of the dialysis liquid in such a manner that these containers may be switched sequentially into the circulatory system by means of valves which are connected into the inflow and outflow of these storage containers whereby the operation of the valves is controlled by an automatic timer.

According to a further embodiment of the invention, the storage containers may be connected at one end thereof through valves with a feeder container of fresh dialysis liquid and at the other end thereof to a discharge conduit for the removal of used-up dialysis liquid.

According to the invention a dosing pump may be used for branching off a desired liquid quantity from the main dialysis circulatory system.

A timer control mechanism is provided which controls the operation of the main pump for the circulatory system. The same control mechanism may control the operation of the branching off pump in a closed loop manner in response to a measurement of the quantity of a branched-off dialysis liquid portion. As mentioned, the automatic timer also controls the valve groups. Such timers are well known in the art.

BRIEF FIGURE DESCRIPTION

In order that the invention may be clearly understood, it will now be described, by way of example, with reference to the accompanying drawings, wherein.

DETAILED DESCRIPTION OF PREFERRED EXAMPLE EMBODIMENTS

Figure 1:
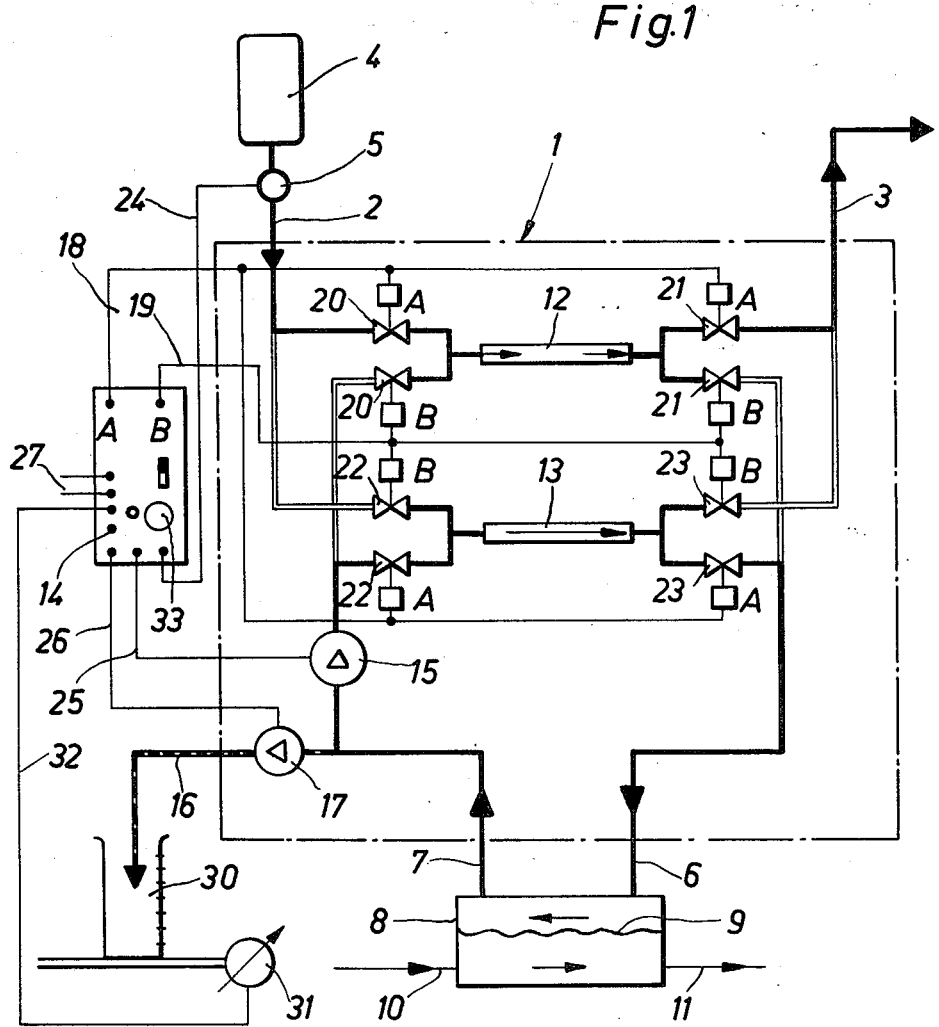
FIG. 1 shows a schematic illustration of an apparatus according to the invention.

The apparatus 1 according to the invention shown in FIG. 1 of the drawings comprises a supply conduit 2 for the dialysis liquid and a discharge conduit 3 for used-up dialysis liquid. The dialysis liquid may be produced in the customary manner by mixing a concentrate and water in a feeder container 4. The dialysis liquid is degassed in the feeder container 4 and heated to body temperature (37° C.). The liquid is fed under light pressure, for example, by means of a supply pump 5, into the supply conduit 2 from the feeder container 4.

In addition, the apparatus according to the invention comprises an output conduit 6 and a return conduit 7. A conventional dialyser 8 is operatively connected to the conduits 6 and 7. The dialyser comprises a semi-permeable membrane 9 which divides the dialyser into two spaces. The dialysis liquid flows through the conduits 6 and 7 and through one of the spaces whereas the blood of the patient is made to flow through the other space in counter-current fashion through the connecting conduits 10 and 11.

According to the invention several storage containers are operatively connectable into the dialysis circulatory system. In the illustrated example embodiment two storage containers 12 and 13 are connected in parallel to each other and to the supply conduit 2 as well as to the discharge conduit 3. The flow through said storage containers is controlled by means of two groups of valves A and B. All valves of the group A are simultaneously actuated as a group. All the valves of group B are also simultaneously actuated in the same manner, however, in an opposite sense to the respective other valve group. Thus, it is possible to use a common drive for both valve groups, for example, in the form of an electromagnetic drive, an electromotor, or in the form of a hydraulic drive. Such valves are well known in the art. For example, electromagnetically operated valves are equipped with solenoids which may be easily energized and de-energized in a timed sequence.

A control mechanism 14 is provided for the time sequence control of the valves and of further components to be described below. The timer mechanism as such is also well known in the art, for example in the form of an integrated circuit (e.g. type 555 of Signetics Corp.) which can directly generate the desired wave form.

A main pump 15 is also connected into the circulatory system of the dialyser 8, namely, in the illustrated embodiment into the return conduit 7. A branching conduit 16 is connected to the return conduit 7. A branching off pump 17 is connected to the branching conduit 16.

Figure 3:
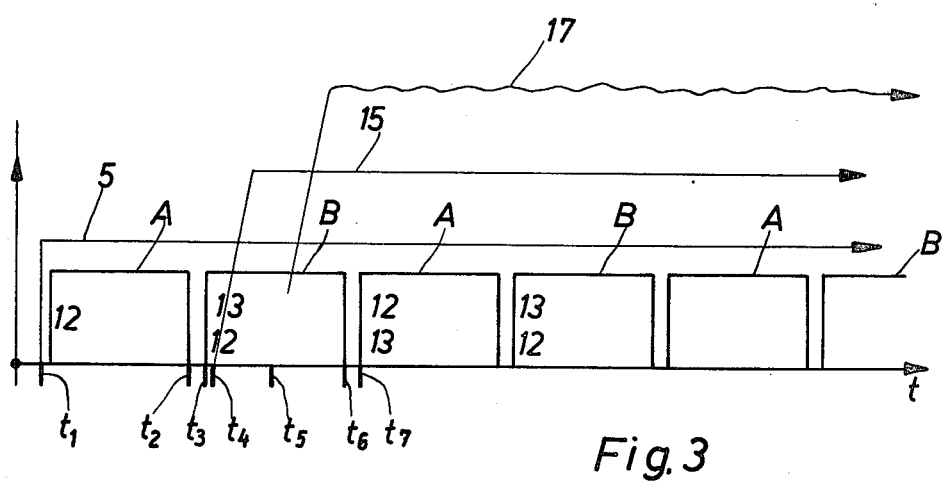
FIG. 3 is a timing diagram of the control function.

The operation of the example embodiment according to FIG. 1 will now be described with reference to the timing diagram of FIG. 3.

Initially it shall be assumed that the apparatus is switched off. In this condition all pumps are in their rest condition and the valves of the groups A and B are closed.

If now the apparatus is switched on at the time $t_1$ the supply pump 5 begins to work, whereby it drives the liquid from the feeder container 4 into the conduit 2. Simultaneously or immediately thereafter, a signal from the control mechanism 14 is supplied through a control conductor 18 to the valves of group A. The valves of group B remain closed at this time. This means that dialysis liquid is slowly introduced into the storage container 12 through the conduit 2 and through the valve 20A. At a predetermined point of time the container is filled and the discharge conduit 3 is filled beyond the valve 21A. The timing in the control mechanism 14 is so determined that a sufficient quantity of dialysis liquid is conveyed by the pump 5. Then, at the time $t_2$ a signal is supplied through the control conductor 18 for closing the valves of group A. The storage container 12 is filled now. The valves A and B now remain closed for a very short period of time and a signal is then supplied to the valves of the group B at the point of time $t_3$. The signal is supplied through a control conductor 19 to the valves of group B which are now opened. The dialysis liquid now flows, fed by the supply pump 5 through the conduit 2 and through the valve 22B into the storage container 13 until the latter is filled and an excess may flow off through the valve 23B. Incidentally, FIG. 1 illustrates with the heavier conduit lines that liquid is flowing therethrough, whereas the double lines indicate that there is no flow in these conduits at the point of time illustrated in FIG. 1 with the valves of group A open and the valves of group B closed.

As soon as the filling of the storage container 13 begins with the valves B open and valves A closed, the main pump 15 is switched on at a point of time $t_4$. The main pump 15 now feeds liquid through the open valves 20B, container 12, valve 21B, conduit 6 into and through the dialyser 8 and through the conduit 7 back into the storage container 12. As soon as this main circulatory system of the dialysis solution becomes operational, the control mechanism 14 switches on the branching pump 17 at the time $t_5$. The pump 17 now feeds a small proportion of liquid out of the conduit 7 and through the conduit 16 into a container 30. The container 30 is connected to a measuring device, for example, a weighing scale 31 which permits measuring or determining the quantity of branched-off dialysis liquid. In the illustrated example embodiment said measuring device 31 is connected with the control mechanism 14 through a control conductor 32. The control mechanism causes the branching off of a predetermined quantity of used-up dialysis liquid as a function of the passing time. As soon as this value is reached at a point of time, the pump 17 is either switched off for a short time, or it is controlled to work slower. This is indicated in the diagram of FIG. 3 in that the time curve for the pump 17 is not shown as a straight line, but rather, as a wavy line to indicate the instantaneous operational condition that is the feeding velocity of the pump 17.

The desired feeding quantity of the pump 17 may be adjusted by means of a control button 33 which is part of the control mechanism and involves a pump speed control well known in the art.

The control mechanism 14 is connected to the pump 5 by a control conductor 24, to the pump 15 by a control conductor 25 and to the pump 17 by a control conductor 26. The control mechanism 14 is supplied with current by means of conductors 27.

In the further course of time the valve group B is closed again at the time $t_6$ whereby the supply of dialysis liquid into the storage container 13 is interrupted. In addition, the circulatory system between the storage container 12 and the dialyser 8 is interrupted. At a shortly following point of time $t_7$ the storage container 13 is connected through the valves 22A and 23A into the circulatory system of the dialyser and the storage container 12 is connected through the valves 20A and 21A to the supply conduit 2 and to the discharge conduit 3. This condition is illustrated in FIG. 1 by the heavy black conduits carrying a liquid flow. Thus, the pump 5 feeds under pressure fresh dialysis liquid slowly supplied through the conduit 2 into the storage container 12, whereby the dialysis liquid used-up in the preceding dialysis operation and now present in the storage container 12 is displaced through the discharge conduit 3.

It is apparent that the supply of the fresh dialysis liquid must take place so slowly that mixing of these two liquids in the container does not occur, or rather, that the mixing occurs only at a boundary zone which is displaced out through the valve 21A toward the end of the filling operation into the the discharge conduit 3. This operation presumes, that a laminar flow is established in the storage container and that eddying is substantially prevented. For this purpose the invention teaches that the storage containers 12 and 13 have an elongated form. Stated differently, these containers have a length very much larger than their diameter. It has been found that a ratio of diameter to length within the range 1:10 to 1:30 is satisfactory for maintaining a substantially laminar flow in the storage containers 12, 13.

Figure 2:
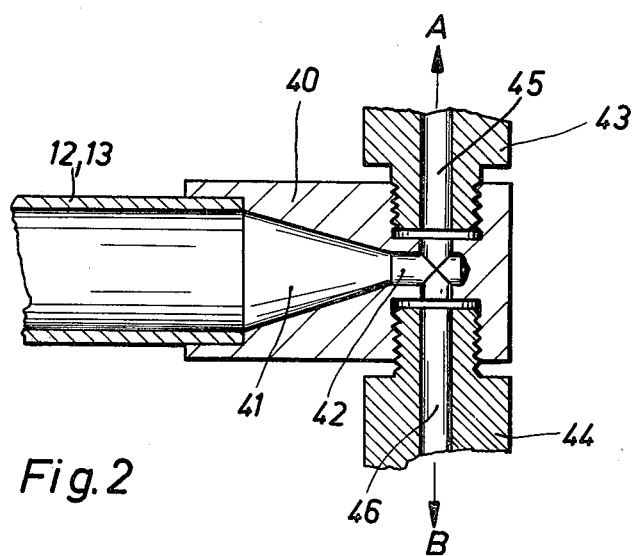
FIG. 2 is a sectional view through the ends of the storage container.

Further, it is necessary that the adapter pieces 40 between the storage containers 12 and 13 proper and the conduits connected thereto, are constructed in a flow facilitating manner. FIG. 2 illustrates one respective example embodiment in which the adapter piece 40 exhibits a slightly conical shape of the flow channel 41 which merges into a conduit section 42.

The connector pieces 43 and 44 to the valves are screwed into the adapter piece 40. The connector pieces 43 and 44 comprise conduits 45 and 46 respectively.

With further passage of time the valves A are closed again and the valves B are opened so that the storage container 13 is filled while simultaneously the storage container 12 is connected into the main circulatory system of the dialyser. These operational steps are repeated automatically under the control of the control mechanism 14 to the end of the dialysis process when the apparatus is switched off.

It is apparent that instead of the weighing device 31 schematically shown in FIG. 1 for the container 30, an optically operating measuring device may be provided, for example, measuring barriers.

Accordingly, the invention is not limited to the illustrated and described example embodiment. Rather, further example embodiments are possible within the teaching of the invention. The containers 12 and 13 which have been called "storage containers" above have a volume up to a maximum of 0.2 liters when the total throughput quantity is about 4 liters of dialysis liquid. Thus, these containers would better be called "working containers".

Although the invention has been described with reference to specific example embodiments, it is to be understood, that it is intended to cover all modifications and equivalents within the scope of the appended claims.

What is claimed is:

1. An apparatus for continuously controlling the liquid flow in a single pass hemodialysis treatment system, comprising at least two elongated container means (12, 13) for the unidirectional and laminar supply of fresh dialysate and for the unidirectional and laminar discharge of used dialysate, each said container means having a given length and a given diameter substantially smaller than the length, whereby the filling and emptying of said elongated container means advances with a unidirectional, laminar flow which moves always in the same direction in said container means, each container means having inlet means at one end thereof and outlet means at the opposite end thereof, said unidirectional flow flowing in each container from said inlet means to said outlet means during filling and during emptying, each of said inlet means and each of said outlet means comprising branching conduit means connected to the respective end of the corresponding container means, controllable valve means operatively interposed in each of said branching conduit means, dialysis liquid feeder container means (4) and feeder conduit means operatively connecting said feeder container means (4) to each inlet means through the respective valve means (20A, 22B) for providing fresh dialysis liquid to said inlet means, discharge conduit means (3) operatively connected to each of said outlet means through the respective valve means, dialyzer means (8, 9) having dialyzer inlet means and dialyzer outlet means for dialysis liquid, first circulatory conduit means (6) operatively connecting each outlet of said elongated container means through the respective valve means to the dialyzer inlet means, second circulatory conduit means (7) operatively connecting each inlet of said elongated container means to said dialyzer outlet means, circulatory pump means (15) operatively interposed in said second circulatory conduit means (7), said first and second circulatory conduit means (6, 7), said circulatory pump means (15) with the respective valve means and one of said container means forming a closed circulatory loop, said circulatory pump means for unidirectional pumping through said closed circulatory loop, control means (14), including conductor means (18, 19) operatively connected for controlling said controllable valve means to alternately connect said elongated container means in timed sequence into said closed circulatory loop said control means for causing at any time at least one of said elongated container means to be connected in said closed circulatory loop while at least one other elongated container means is connected between said dialysis liquid feeder container means (4) and said discharge conduit means so as to discharge used dialysis liquid without recirculation to said dialyzer means and for causing the reversal of said connections such that at the beginning of an operating phase at least one container is filled with fresh dialysis liquid and at least another continner is filled with used-up dialysis liquid and this filling status is reversed at the end of said operating cycle so that used-up and fresh dialysis liquid will not be mixed; branching pump means (17) operatively connected to said second circulatory conduit means (7) upstream of said circulatory pump means (15) for withdrawing liquid from said closed circulatory loop, liquid quantity measuring means (30, 31) operatively connected to said branching pump means for measuring dialysis liquid withdrawn per unit of time from said closed circulatory loop by said branching pump means, said liquid quantity measuring means producing a feedback control signal proportional to the withdrawn dialysis liquid, and closed loop feedback means (32, 26) operatively controlling the operation of said branching pump means in closed loop feedback fashion in response to the withdrawn proportion of dialysis liquid.

2. The apparatus of claim 1, further comprising supply pump means (5) operatively connected in said feeder conduit means, said circulatory pump means (15) and said supply pump means (5) working in such a direction that liquid flows in the same direction through both of said elongated working container means, whereby a boundary zone between liquid entering the working container means and liquid discharging from the working container means is established, said boundary zone travelling from said working container inlet means to said working container outlet means.

3. The apparatus of claim 1, wherein said diameter of said working container means to the length of said working container means is within the range of 1 to 10 to 1 to 30.

4. The apparatus of claim 1, wherein said closed loop feedback means comprise electrical control conductor means (25, 26) operatively connecting said circulatory pump means (15) and said branching pump means (17) to said control means, further conductor means (32) connecting said liquid measuring means (30, 31) to said control means (14) for measuring a predetermined proportion of withdrawn liquid to produce said feedback control signal for said branching pump means (17) and for said circulatory pump means (15).

5. The apparatus of claim 1, further comprising diameter adapter means operatively connecting the respective working container means to the respective controllable valve means.

6. The apparatus of claim 1, wherein said branching pump (17) is constructed as a dosing pump capable of delivering a desired feeding quantity or dosage with each operational step.

* * * * *